United States Patent [19]
Tamano et al.

[11] Patent Number: 5,948,941
[45] Date of Patent: *Sep. 7, 1999

[54] MATERIAL FOR ORGANOELECTROLUMINESCENCE DEVICE AND ORGANOELECTROLUMINESCENCE DEVICE USING THE MATERIAL

[75] Inventors: Michiko Tamano; Toshikazu Onikubo; Satoshi Okutsu; Toshio Enokida, all of Tokyo, Japan

[73] Assignee: Toyo Ink Manufacturing Co., Ltd., Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/990,193

[22] Filed: Dec. 12, 1997

[30] Foreign Application Priority Data

Dec. 16, 1996 [JP] Japan ..................................... 8-335217
Nov. 4, 1997 [JP] Japan ..................................... 9-301457

[51] Int. Cl.$^6$ .................................................. C07C 211/00
[52] U.S. Cl. ............................................. 564/315; 430/73
[58] Field of Search ................................ 564/315; 430/73

[56] References Cited

U.S. PATENT DOCUMENTS 4,789,336 12/1988 Rule ......................................... 564/315
4,920,022 4/1990 Sakakibara et al. ....................... 430/59
5,508,136 4/1996 Shirota et al. ............................. 430/73
5,573,878 11/1996 Hagiwara et al. ......................... 430/59

FOREIGN PATENT DOCUMENTS 0 508 562  10/1992  European Pat. Off. .
0 517 542  12/1992  European Pat. Off. .
0 611 148  8/1994   European Pat. Off. .
195 41 113  4/1997  Germany .

OTHER PUBLICATIONS

Stickley et al., "Cation Radicals of 1,3,5–Tris(diarylamino)benzenes",*Tetrahedron Letters,* vol. 36, No. 10, Mar. 6, 1995, pp. 1585–1588.

Shirota et al., "Multilayered Organic Electroluminescent Device Using a Novel Starburst Molecule, 4,4',4"–Tris (3–methylphenylphenylamnino)Triphenylamine, As A Hole Transport Material,*Applied Physics,* vol. 65, No. 7, Aug. 15, 1994.

Ishikawa et al., "Novel Amorphous Molecular Materials; The Starburst Molecule 1,3,5–Tris(N–(4–Diphenylaminophenyl)Phenyl Lamino)Benzene",*Advanced Materials,* vol. 5, No. 7/08, Jul. 1, 1993.

*Primary Examiner*—Samuel Barts
*Attorney, Agent, or Firm*—Wenderoth, Lind & Ponack, L.L.P.

[57] ABSTRACT

A material for an organic EL device, having excellent capability of injecting holes from a metal electrode and having durability, and an organic EL device which is imparted with excellent stability in the repeated use for light emission by using the above material, the material having the formula (1), (6) or (7) as specified in claim 1.

7 Claims, 1 Drawing Sheet

MATERIAL FOR ORGANOELECTROLUMINESCENCE DEVICE AND ORGANOELECTROLUMINESCENCE DEVICE USING THE MATERIAL

FIELD OF THE INVENTION

The present invention relates to a material having a triphenylamine structure, used for the production of an electroluminescence device (EL device), and an organic EL device using the above material, and more specifically, it relates to a material having a triphenylamine structure, used as a hole-injecting material for the production of an organic EL device for use as a planar light source or display, and an organic EL device using the above material.

PRIOR ART

Organic photo-conductive materials which have been developed as photosensitive materials or hole-injecting materials are advantageously less expensive, easily processible and free from causing pollution, and a variety of compounds have been proposed. Examples of the disclosed organic photo-conductive materials include oxadiazole derivatives (U.S. Pat. No. 3,189,447), oxazole derivatives (U.S. Pat. No. 3,257,203), hydrazone derivatives (U.S. Pat. No. 3,717,462, JP-A-54-59,143, U.S. Pat. No. 4,150,978), triaryl pyrazoline derivatives (U.S. Pat. No. 3,820,989, JP-A-51-93,224, JP-A-55-108,667), arylamine derivatives (U.S. Pat. No. 3,180,730, U.S. Pat. No. 4,232,103, JP-A-55-144,250, JP-A-56-119,132), and stilbene derivatives (JP-A-58-190,953, JP-A-59-195,658).

An organic EL device is one technical example to which the hole-injecting material is adapted. An EL device using an organic substance is greatly expected to be usable as a solid light-emitting inexpensive large-screen, full-color display device, and developments thereof are being made in many ways. Generally, an organic EL device is composed of a light-emitting layer and a pair of mutually opposite electrodes sandwiching the light-emitting layer. The light emission by an EL device is based upon the following phenomenon. When an electric field is applied between the two electrodes, the cathode injects electrons into the light-emitting layer, and the anode injects holes into the light-emitting layer. Further, when the electrons recombine with the holes in the light-emitting layer, their energy level shifts from a conduction band back to a valence electron band to release energy as light.

As compared with inorganic EL devices, conventional organic EL devices require high voltage for its activation, and further, their light emission brightness and light emission efficiency are low. Further, conventional organic EL devices deteriorate in properties to a great extent, and no organic EL device has been put to practical use.

There has been recently proposed an organic EL device which is produced by laminating a thin film containing an organic compound having a fluorescent quantum effect to emit light at a low voltage as low as less than 10 V, and it attracts attention (Appl. Phy. Lett., Vol. 51, page 913, 1987).

The above organic EL device has a fluorescent layer containing a metal chelate complex and a hole-injecting layer containing an amine-based compound, and emits green light having a high brightness. The above organic EL device achieves a brightness of 100 cd/m$^2$ and a maximum light emission efficiency of 1.5 lm/W at a direct current voltage of 6 or 7 V and thus has nearly practically usable performance.

An organic EL device has a structure in which a light-emitting layer containing an organic fluorescent compound is provided between a metal cathode layer and a transparent anode layer. Further, an electron-injecting layer and a hole-injecting layer are provided for obtaining light emission having a high brightness at a low voltage. In the organic EL device, electrons injected from a cathode and holes injected from an anode are recombined to generate excitons and the excitons radiate light in the process of radiation and deactivation thereof (JP-A-59-194393, JP-A-63-295695). However, when the device continues to emit light in the continuous operation under the application of direct current for a long period of time, crystallization in the organic compound is promoted etc., and leak current is liable to occur in the device so that the device is liable to be eventually broken. For overcoming the above problem, a compound such as 4,4',4"-tris(N,N'-diphenylamino)triphenylamine (TDATA) or 4,4,,4"-tris[N-(3-methylphenyl)-N-phenylamino]-triphenylamine (MTDATA) is used as a hole-injecting material for use in a hole-injecting layer (JP-A-4-308688). The above compounds have effects that they are less crystallizable owing to the twisted steric form of their molecules and are excellent in thin film formability. However, these compounds have a glass transition point of about 70° C., a melting point of about 200° C. and a decomposition temperature of about 340° C. and thus have no sufficient heat resistance. There is therefore a problem, when the device using the above compounds is light-emitted, the device is easily deteriorated by Joule's heat generated in the device.

As discussed above, the organic EL devices which have been so far developed are not sufficient in light emission brightness and light emission stability in the repeated use for light emission. It is therefore desired to develop a hole-injecting material having excellent hole-injecting capability and durability for attaining an organic EL device having a higher light emission brightness, a high light emission efficiency and excellent stability in the repeated use for light emission.

SUMMARY OF THE INVENTION

It is an object of the present invention to provide a material for an organic EL device, which material has excellent capability of injecting holes from a metal electrode and has durability.

It is another object of the present invention to provide an organic EL device which is imparted with excellent stability in the repeated use for light emission by using the above material.

According to the present invention, there is provided a material for an organic EL device, which has the formulae (1), (6) or (7),

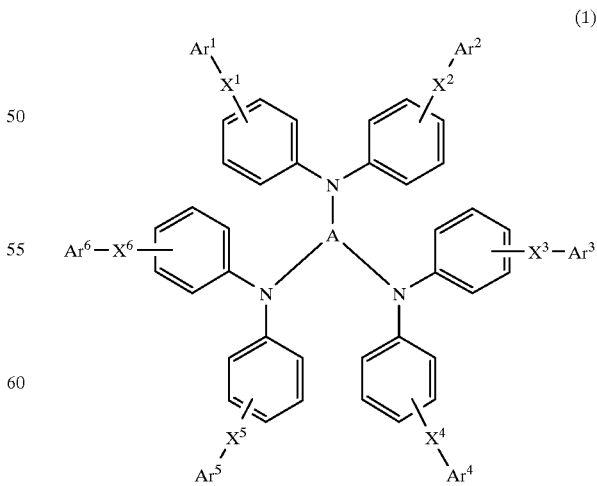

wherein each of $Ar^1$ to $Ar^6$ is independently a substituted or non-substituted aryl group, each of $X^1$ to $X^6$ is independently —O—, —S—, >C=O, >SO$_2$—Si(B$^1$)B$^2$—, —N(B$^1$)—, —PB$^1$—, —P(=O)B$^1$—, —(CH$_2$)$_x$—O—(CH$_2$)$_y$—, a substituted or non-substituted alkylene group, a substituted or non-substituted alicyclic moiety, in which each of B$^1$ and B$^2$ is independently a substituted or non-substituted alkyl group or a substituted or non-substituted aryl group and each of x and y is an integer of 0 to 20, provided that x+Y=0 in no case, and A is a group having one of the following formulae,

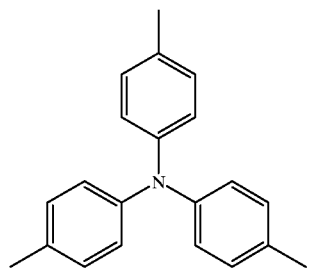

(2)

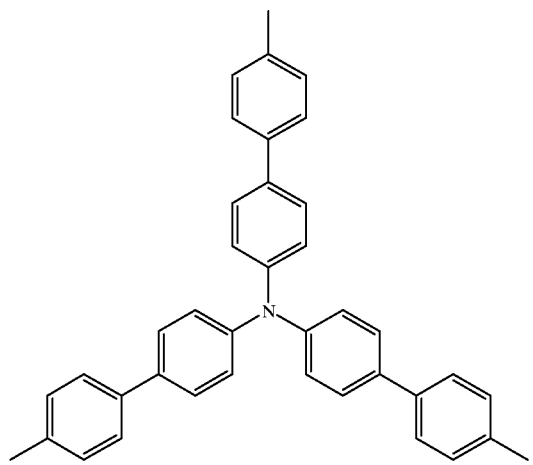

(3)

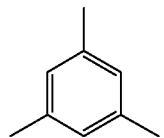

(4)

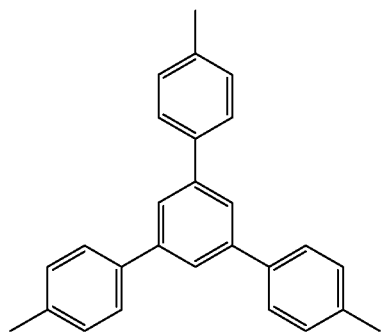

(5)

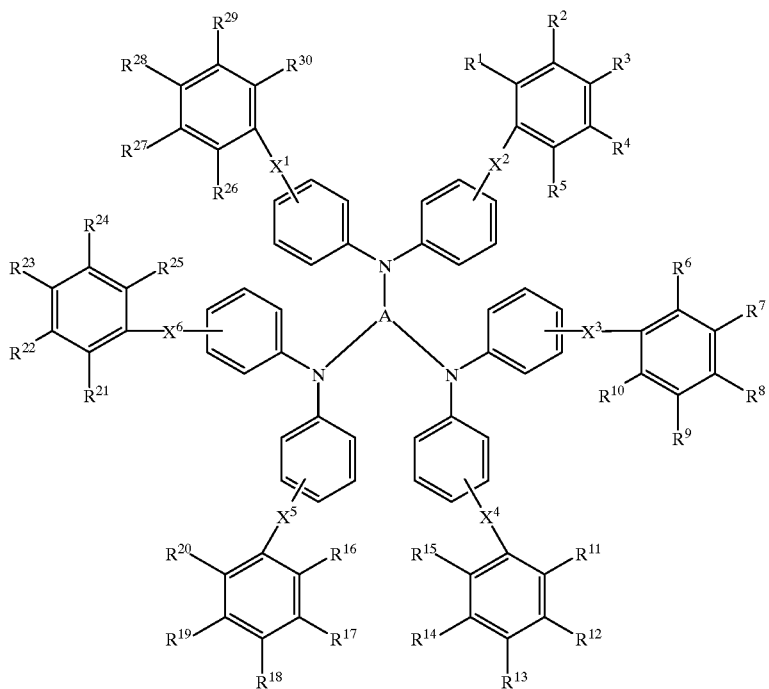
(6)
wherein each of $R^1$ to $R^{30}$ is independently a hydrogen atom, a halogen atom, a substituted or non-substituted alkyl group, a substituted or non-substituted alkoxyl group, a substituted or non-substituted aryl group or a substituted or non-substituted amino group, and $X^1$ to $X^6$ and A are as defined in the formula (1),
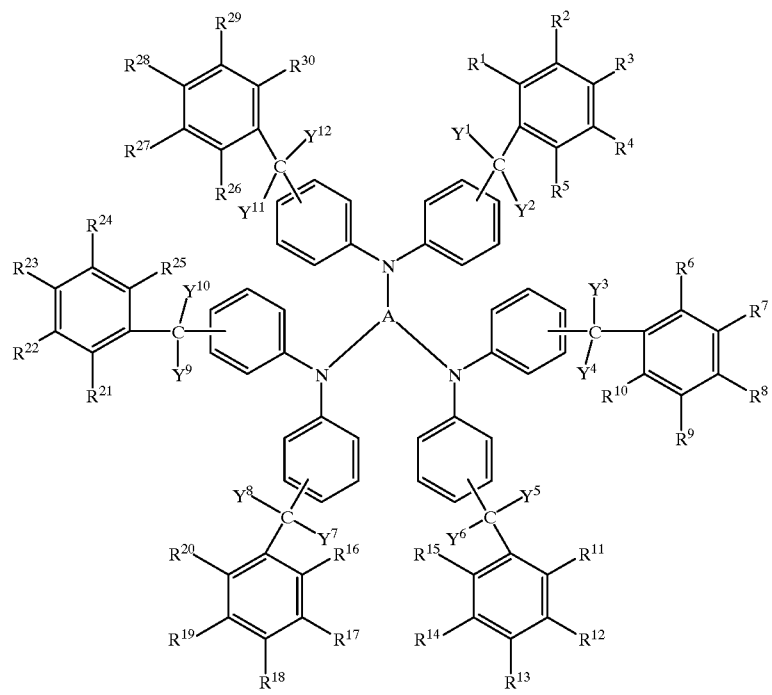
(7)

wherein each of $R^1$ to $R^{30}$ is independently a hydrogen atom, a halogen atom, a substituted or non-substituted alkyl group, a substituted or non-substituted alkoxy group, a substituted or non-substituted aryl group or a substituted or non-substituted amino group, each of $Y^1$ to $Y^{12}$ is a substituted or non-substituted alkyl group having 1 to 20 carbon atoms or a substituted or non-substituted aryl group, and A is as defined in the formula (1).

Further, according to the present invention, there is provided an organic EL device obtained by forming either a light-emitting layer or a plurality of organic compound thin layers including the light-emitting layer between a pair of electrodes composed of a cathode and an anode, wherein at least one layer contains the above material of the above formula (1), (6) or (7) as a hole-injecting material.

Further, according to the present invention, there is provided an organic EL device in which at least one organic thin layer between an anode and a light-emitting layer contains the above material for an organic EL device.

Further, according to the present invention, there is provided an organic EL device in which the organic EL device has at least two hole-injecting layers as organic compound thin layers between an anode and a light-emitting layer and each hole-injecting layer contains the above material for an organic EL device.

Further, according to the present invention, there is provided an organic EL device of which the light-emitting layer contains, as a hole-injecting layer, the above material for an organic EL device.

DETAILED DESCRIPTION OF THE INVENTION

Figure 1:
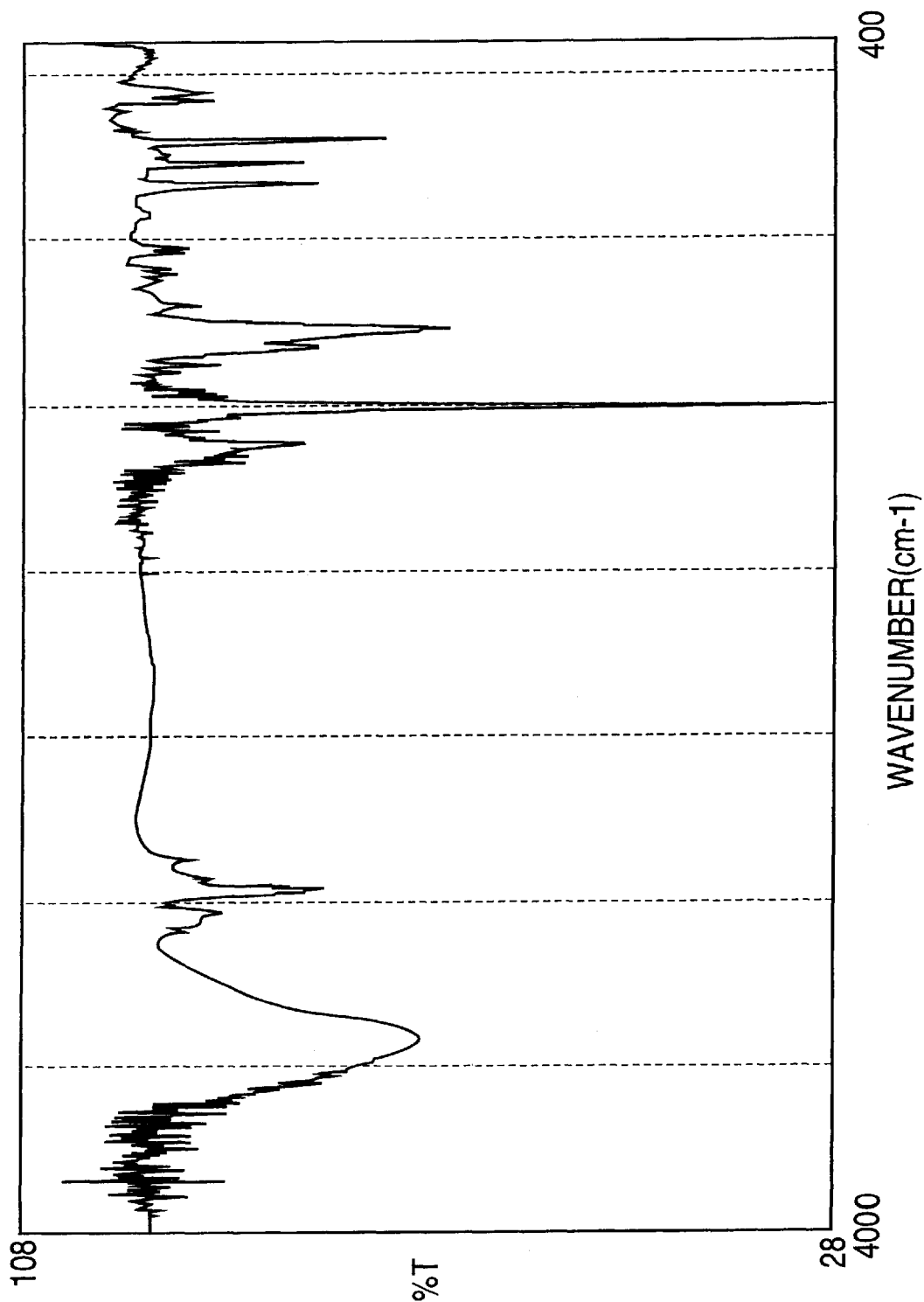
FIG. 1 is an infrared absorption spectrum of Compound 3.

The present inventors have made diligent studies to overcome the above problems, and have found that the hole-injecting material of any one of the formulae (1), (6) and (7), has high hole-injecting capability and gives an organic EL device having excellent device characteristics.

In the formula (1), each of $Ar^1$ to $Ar^6$ is independently a substituted or non-substituted aryl group.

Specific examples of $Ar^1$ to $Ar^6$ include substituted or non-substituted aryl groups such as phenyl, 2-methylphenyl, 3-methylphenyl, 4-methylphenyl, 4-ethylphenyl, biphenyl, 4-methylbiphenyl, 4-ethylbiphenyl, 4-cyclophenoxybiphenyl, terphenyl, 3,5-dichlorophenyl, naphthyl, 5-methylnaphthyl, anthryl and pyrenyl, and aryl groups of which the aromatic hydrocarbon atom may be replaced by a nitrogen atom, an oxygen atom or a sulfur atom, such as furanyl, thiophenyl, pyrrolyl, pyranyl, thiopyranyl, pyridyl, thiazolyl, imidazolyl, pyrimidinyl, tirazinyl, iondolinyl, quinolyl and purinyl. In the above aryl groups, adjacent substituents may bond to each other to form a saturated or unsaturated ring.

In the formulae (6) and (7), each of $R^1$ to $R^{30}$ is independently a hydrogen atom, a halogen atom, a substituted or non-substituted alkyl group, a substituted or non-substituted alkoxyl group, a substituted or non-substituted aryl group or a substituted or non-substituted amino group.

Specifically, the halogen atom includes fluorine, chlorine, bromine and iodine. The substituted or non-substituted alkyl group includes non-substituted linear or branched alkyl groups having 1 to 20 carbon atoms such as methyl, ethyl, propyl, butyl, sec-butyl, tert-butyl, pentyl, hexyl, heptyl, octyl and stearyl, and alkyl groups having 1 to 20 carbon atoms and containing a substituent such as 2-phenylisopropyl, trichloromethyl, trifluoromethyl, benzyl, α-phenoxybenzyl, α,α-dimethylbenzyl, α,α-methylphenylbenzyl, α,α-ditrifluoromethylbenzyl, triphenylmethyl and α-benzyloxybenzyl. The substituted or non-substituted alkoxyl group includes non-substituted alkoxyl groups having 1 to 20 carbon atoms such as alkoxyl, methoxyl, ethoxyl, propoxyl, n-butoxyl, sec-butoxyl, tert-butoxyl, pentyloxyl, hexyloxyl and stearyloxyl, and alkoxyl groups having 1 to 20 carbon atoms and containing a substituent such as 1,1-tetrafluoroethoxyl, phenoxyl, benzyloxyl and octylphenoxyl. The substituted or non-substituted aryl group includes substituted or non-substituted aryl groups of which the aromatic ring or rings have 6 to 18 carbon atoms such as phenyl, 2-methylphenyl, 3-methylphenyl, 4-methylphenyl 4-ethylphenyl, biphenyl, 4-methylbiphenyl, 4-ethylbiphenyl, 4-cyclohexylbiphenyl, terphenyl, 3,5-dichlorophenyl, naphthyl, 5-methylnaphthyl, anthryl and pyrenyl and aryl groups of which the aromatic hydrocarbon atom may be replaced by a nitrogen atom, an oxygen atom or a sulfur atom, such as furanyl, thiophenyl, pyrrolyl, pyranyl, thiopyranyl, pyridinyl, thiazolyl, imidazolyl, pyrimidinyl, Pyridinyl, triazinyl, indolinyl, quinolyl and purinyl. The substituted or non-substituted amino group includes amino, dialkylamino groups such as dimethylamino and diethylamino, phenylmethylamino, diphenylamino, ditolylamino and dibenzylamino. In the above aryl groups, adjacent substituents may bond to each other to form a saturated or unsaturated ring.

In the formula (1), each of $X^1$ to $X^6$ is independently —O—, —S—, >C=O, >SO$_2$, —Si(B$^1$)B$^2$—, —N(B$^1$)—, —PB$^1$—, —P(=O)B$^1$—, —(CH$_2$)$_x$—O—(CH$_2$)$_y$—, a substituted or non-substituted alkylene group or a substituted or non-substituted alicyclic moiety, in which each of $B^1$ and $B^2$ is independently a substituted or non-substituted alkyl group or a substituted or non-substituted aryl group and each of x and y is an integer of 0 to 20, provided that x +Y=0 in no case.

The above substituted or non-substituted alkylene group includes alkylene groups having 1 to 20 carbon atoms and these alkylene groups containing a substituent. The substituted or non-substituted alicyclic moiety includes divalent moieties from aliphatic rings having 5 to 7 carbon atoms such as a cyclopentyl ring, a cyclohexyl ring, a 4-methylcyclohexyl ring and a cycloheptyl ring.

The substituent contained in the substituted alkylene group or the substituted aliphatic moiety in the definition of $X^1$ to $X^6$ includes those substituents specified with regard to $R^1$ to $R^{30}$. The substituted alkylene group for $X^1$ to $X^6$ preferably includes 2-phenyleneisopropylene, dichloromethylene, difluoromethylene, benzylene, α-phenoxybenzylene, α,α-dimethylbenzylene, diphenylmethylene and α-benzyloxybenzylene. Further, the substituted or non-substituted alkyl group and the substituted or non-substituted aryl group in the definition of $B^1$ and $B^2$ specifically include those alkyl groups and aryl groups specified with regard to $R^1$ to $R^{30}$.

In the formula (7), each of $Y^1$ to $Y^{12}$ is a substituted or non-substituted alkyl group having 1 to 20 carbon atoms or a substituted or non-substituted aryl group having 6 to 18 carbon atoms. Specifically, the alkyl group and the aryl group include those alkyl groups and aryl groups specified with regard to $R^1$ to $R^{30}$.

The material of the present invention (i.e., compound of the formula (1), (6) or (7)) can be synthesized, for example, by the following method.

Tris(p-bromophenyl)amine and a substituted aromatic diamine compound are allowed to react in a nitrobenzene solvent in the co-presence of potassium carbonate and a catalyst such as copper or the like at 200° C. for 50 hours, to obtain an aromatic amine compound of the formula (1). The potassium carbonate may be replaced with sodium carbonate, potassium hydroxide or sodium hydroxide. The catalyst is selected from a copper powder, cuprous chloride, tin or stannous chloride. The solvent is selected from 1,3-dimethyl-2-imidazolidinone, N,N-dimethylformamide or dimethylsulfoxide.

Table 1 shows specific examples of the compound of the formula (I), while the compound of the formula (I) shall not be limited thereto.

TABLE 1

| No. | Chemical structure |
|---|---|
| 1 | 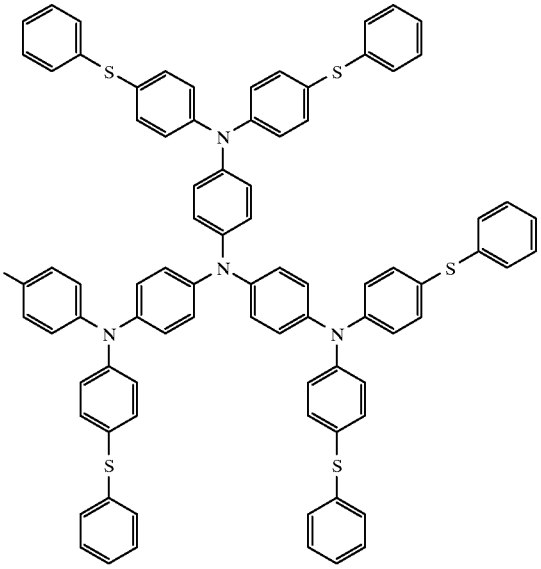 |
| 2 | 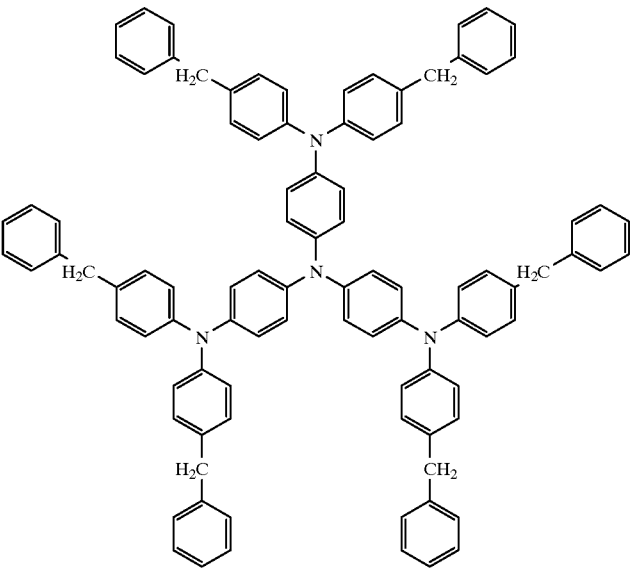 |

TABLE 1-continued
| No. | Chemical structure |
|---|---|
| 3 | 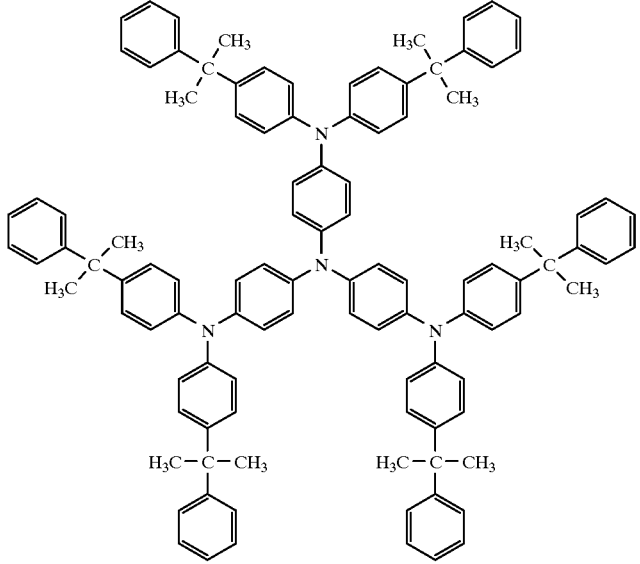 |
| 4 | 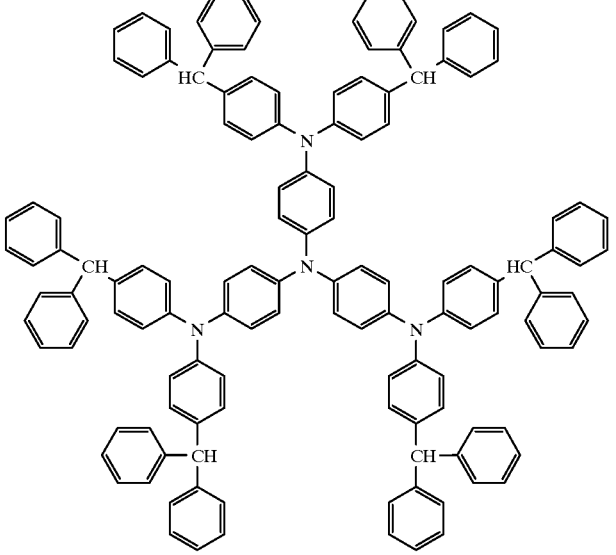 |

TABLE 1-continued
| No. | Chemical structure |
|---|---|
| 5 | 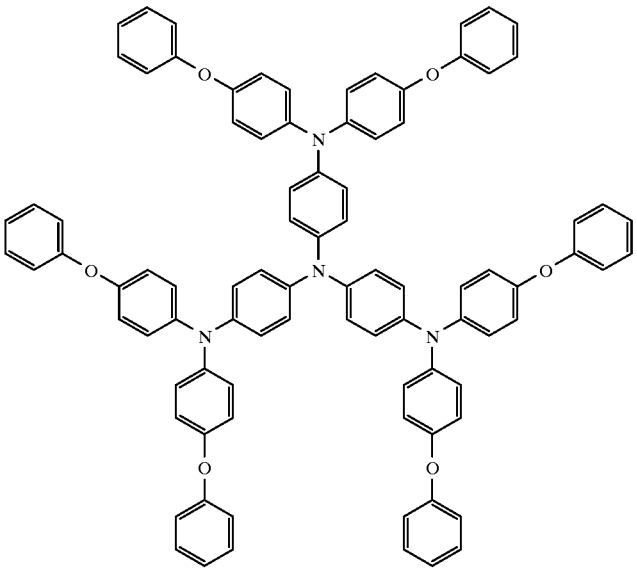 |
| 6 | 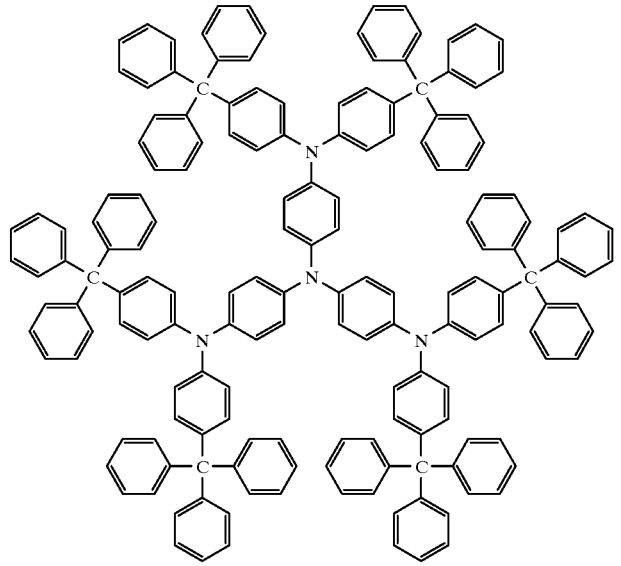 |

TABLE 1-continued
| No. | Chemical structure |
| --- | --- |
| 7 | 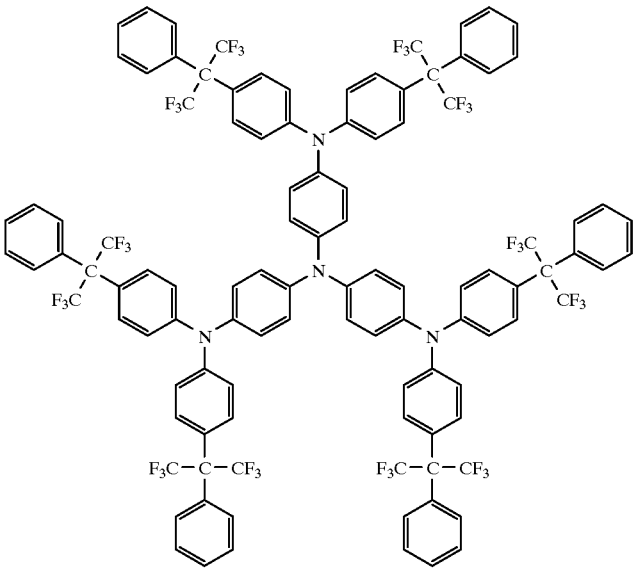 |
| 8 | 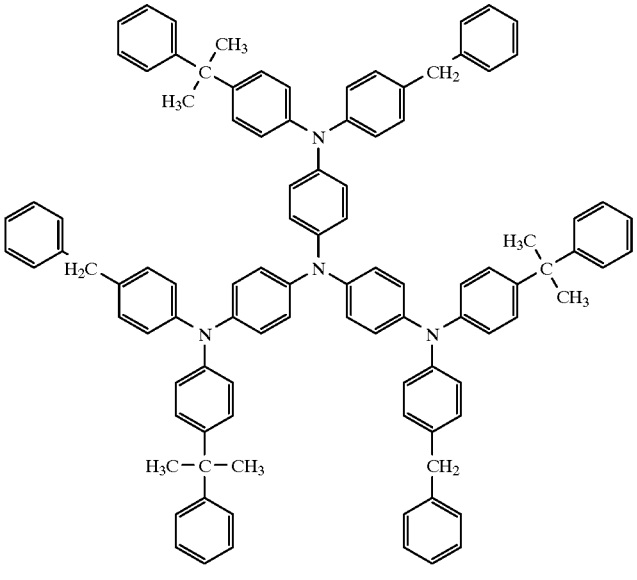 |

TABLE 1-continued
| No. | Chemical structure |
|---|---|
| 9 | 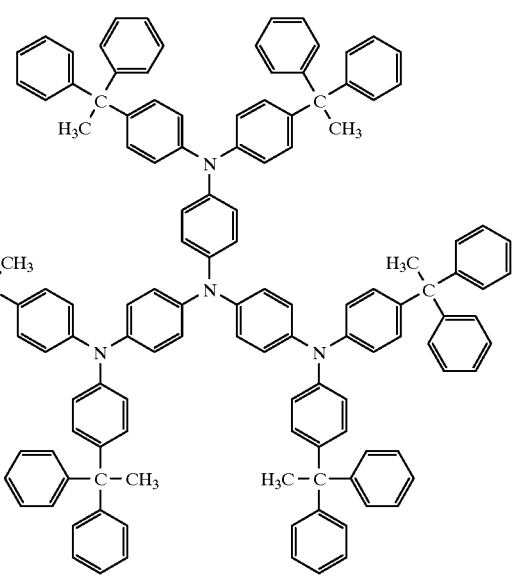 |
| 10 | 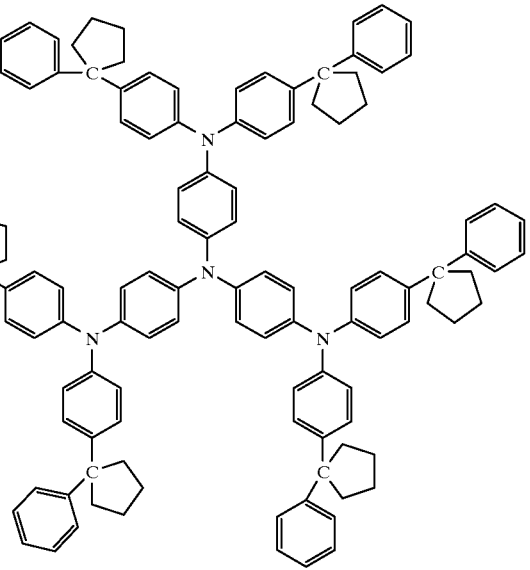 |

TABLE 1-continued

| No. | Chemical structure |
| --- | --- |
| 11 | 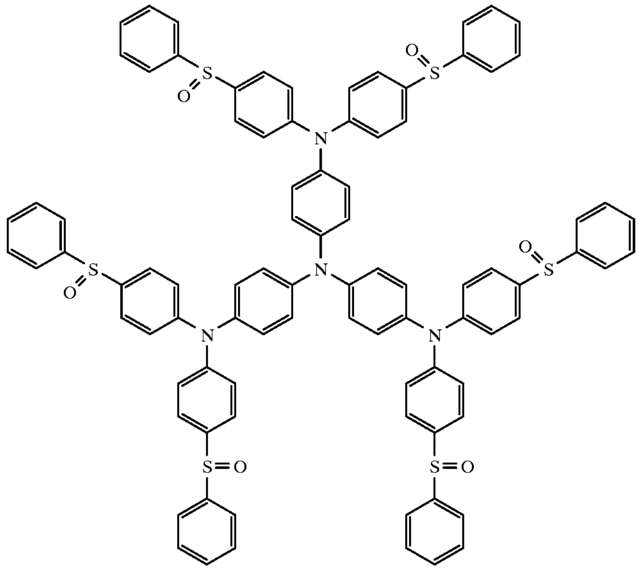 |
| 12 | 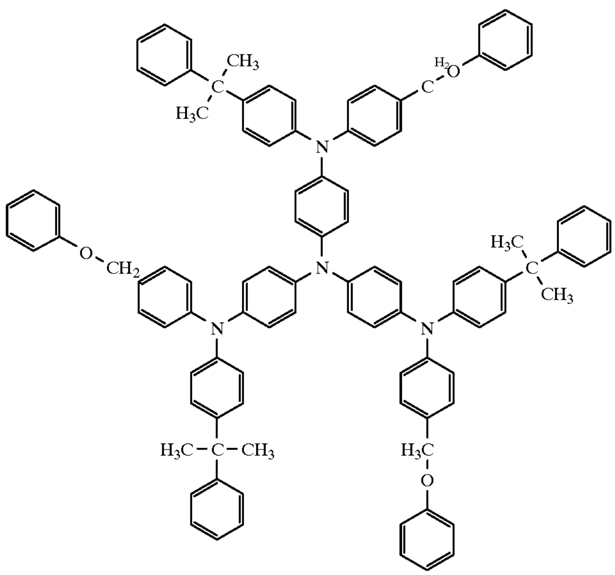 |

TABLE 1-continued
| No. | Chemical structure |
|---|---|
| 13 | 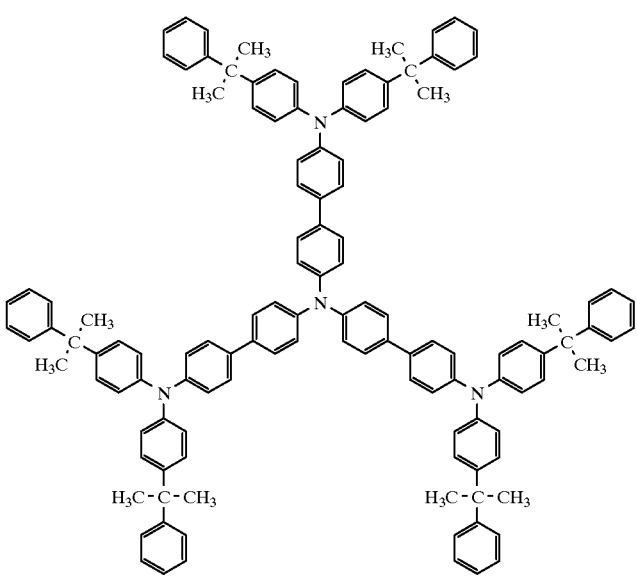 |
| 14 | 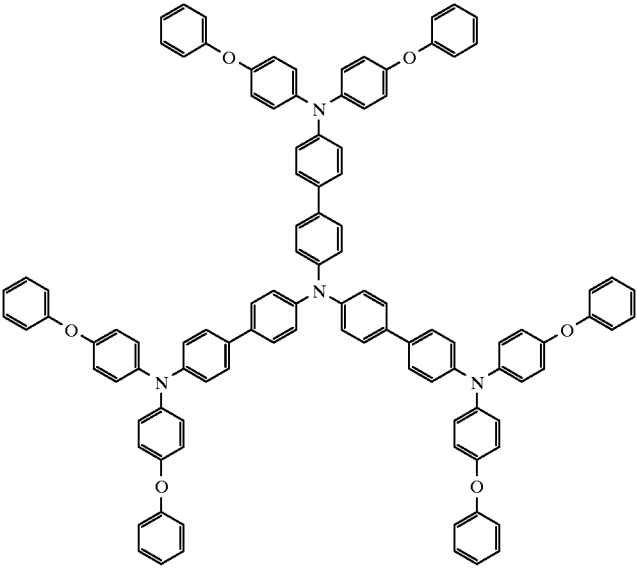 |

TABLE 1-continued
| No. | Chemical structure |
|---|---|
| 15 | 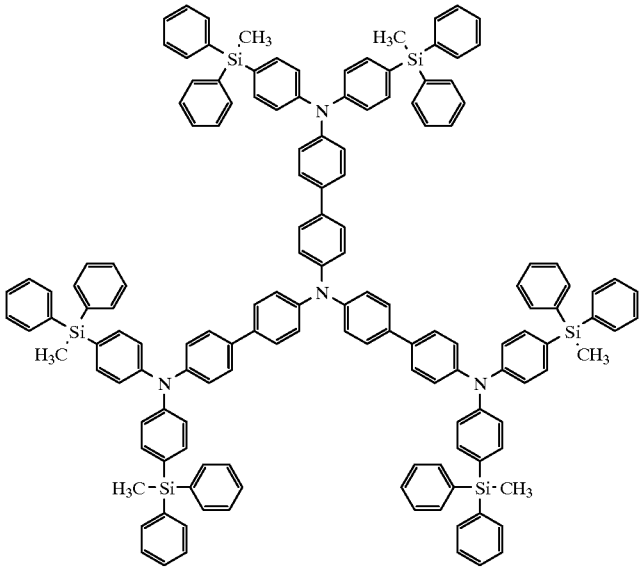 |
| 16 | 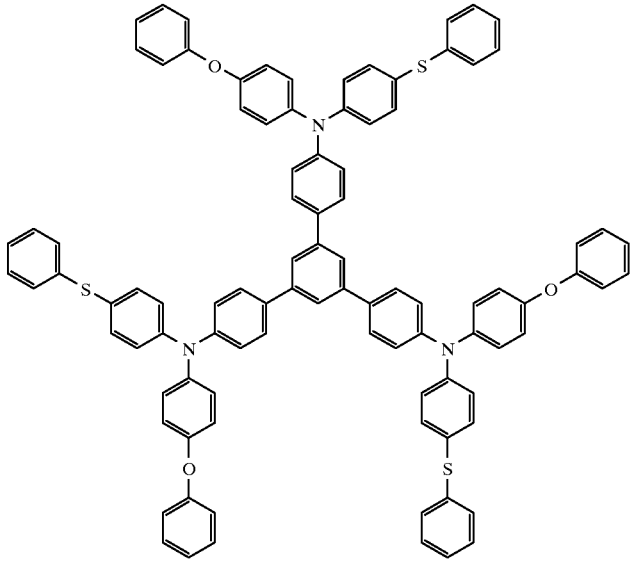 |

TABLE 1-continued

| No. | Chemical structure |
|---|---|
| 17 | 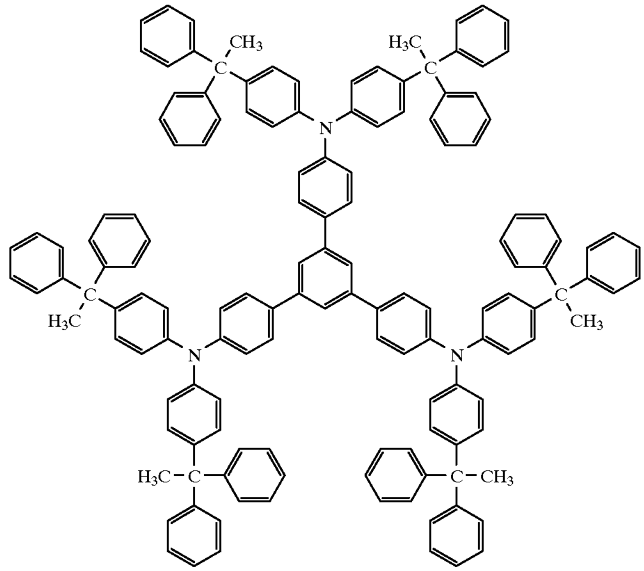 |
| 18 | 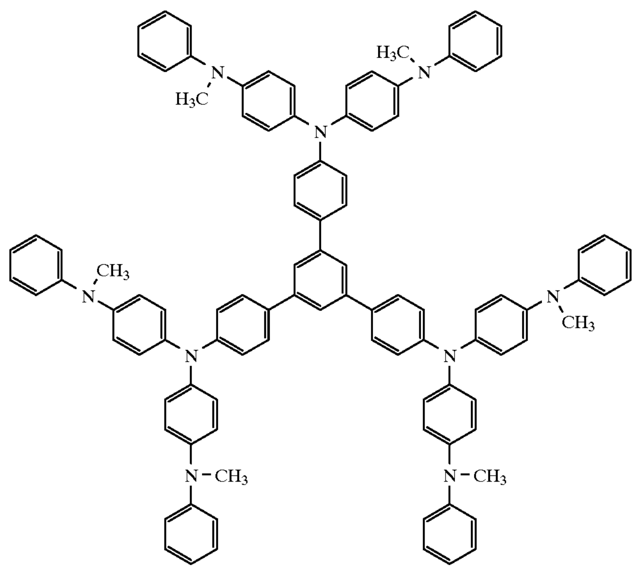 |

TABLE 1-continued
| No. | Chemical structure |
|---|---|
| 19 | 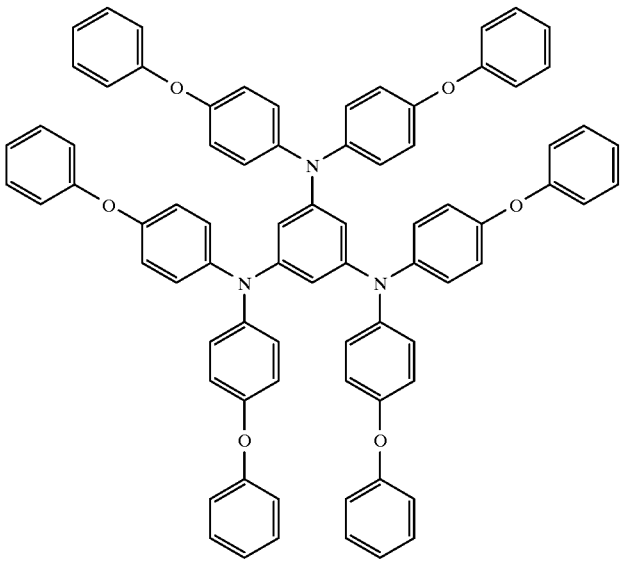 |
| 20 | 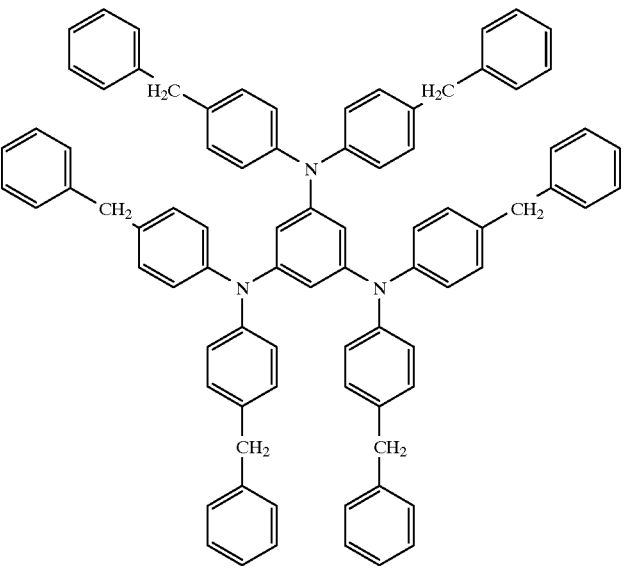 |

TABLE 1-continued
| No. | Chemical structure |
|---|---|
| 21 | 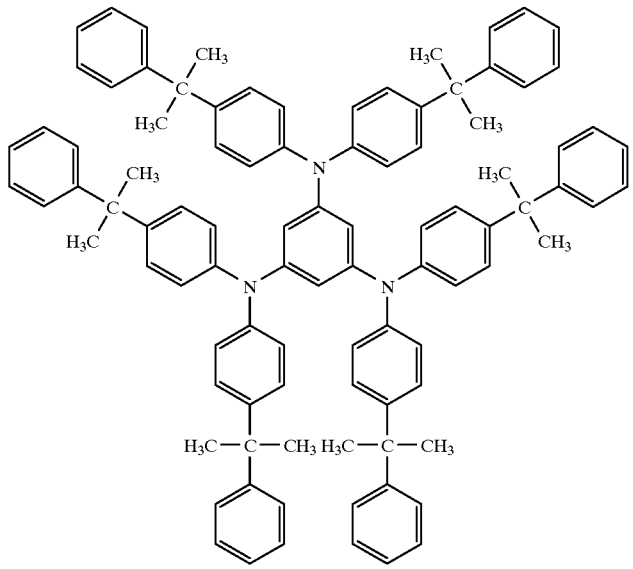 |
| 22 | 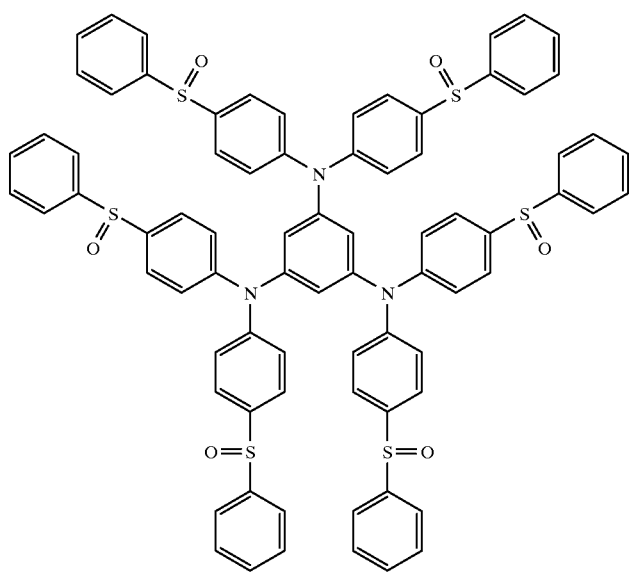 |

TABLE 1-continued
| No. | Chemical structure |
|---|---|
| 23 | 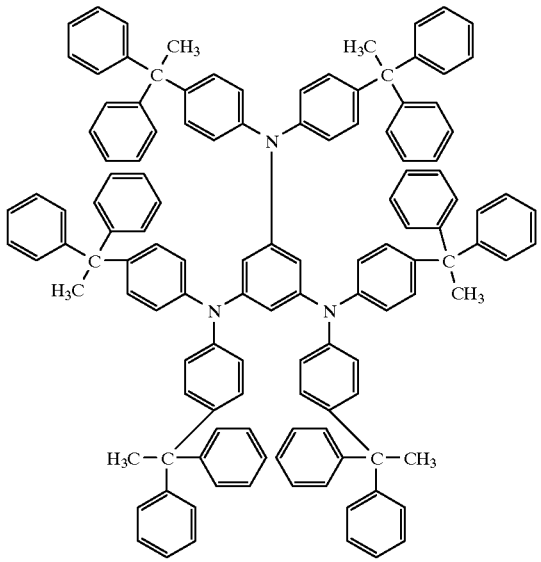 |
| 24 | 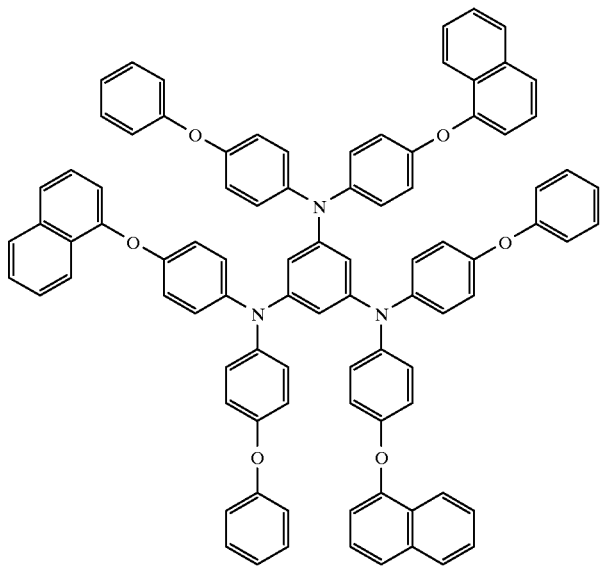 |

TABLE 1-continued
| No. | Chemical structure |
|---|---|
| 25 | 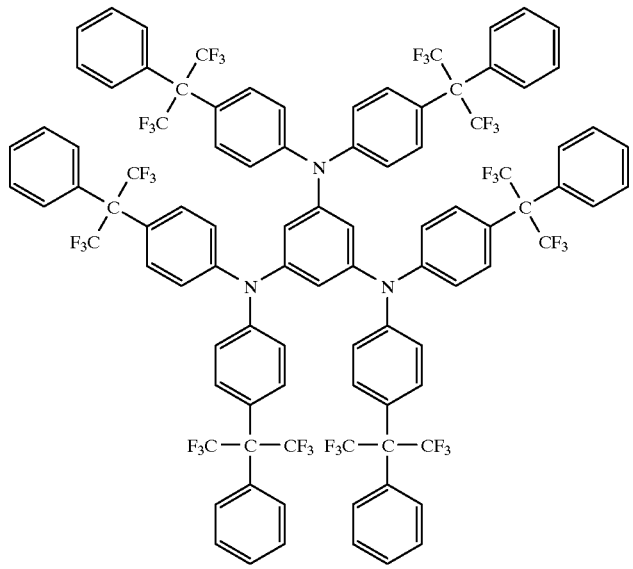 |
| 26 | 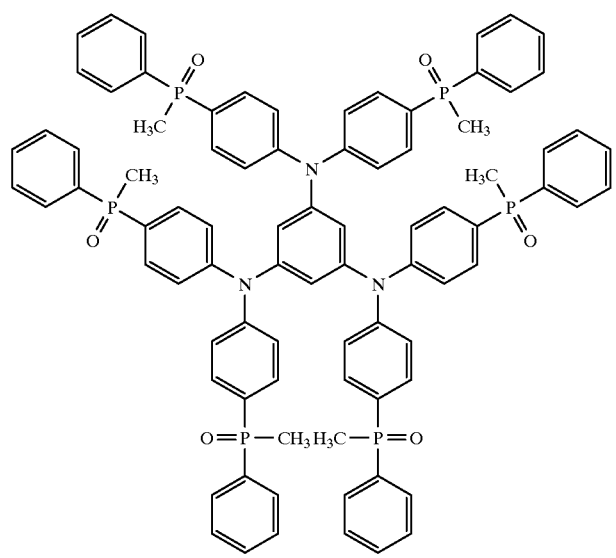 |

TABLE 1-continued

| No. | Chemical structure |
|---|---|
| 27 | 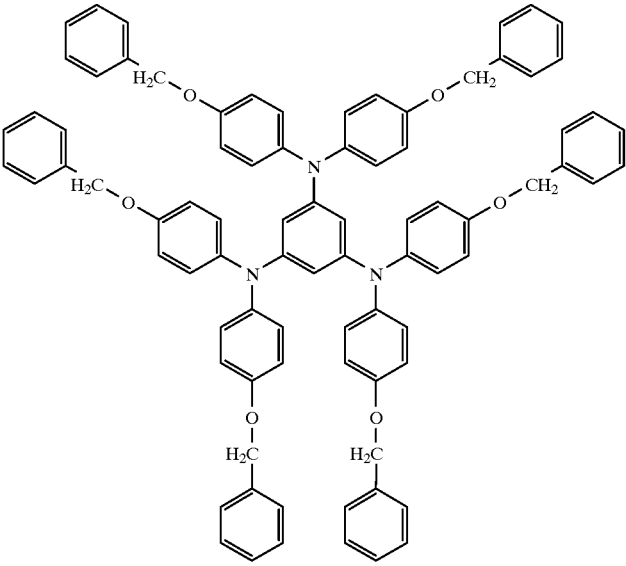 |

The material of the present invention may be used together with other hole-injecting material in one layer. Since the material of the present invention is excellent in the capability of injecting holes, it can be very effectively used as a hole-injecting material.

The organic EL device has a structure in which a mono- or multi-layered organic thin film including a light-emitting layer is formed between an anode and a cathode. In a mono-layered device, a light-emitting layer is formed between the anode and the cathode. The light-emitting layer contains a light-emitting material, and in addition thereto, it may contain a hole-injecting material for transporting holes injected from the anode to the light-emitting material, or an electron-injecting material for transporting electrons injected from the cathode to the light-emitting material. Some light-emitting materials have the capability of injecting holes or electrons. The multi-layered organic EL device has one of laminated-layer structures, for example, of (anode/hole-injecting layer/light-emitting layer/cathode), (anode/light-emitting layer/electron-injecting layer/cathode) and (anode/hole-injecting layer/light-emitting layer/electron-injecting layer/cathode). The material of the present invention (compound of the formula (1), (6) or (7)) can be used in any one of the above device structures. The material of the present invention can be suitably used for any one of the above layer structures. Since the material of the present invention has the high capability of injecting holes, it can be used as a hole-injecting material in any one of the hole-injecting layer and the light-emitting layer.

In addition to the material of the present invention, the light-emitting layer may contain a known light-emitting material, a known dopant, a known hole-injecting material for transporting a carrier or a known electron-injecting material as required. When the organic EL device has a two-layered structure, the light-emitting layer and the hole-injecting layer are separated. Owing to this structure, the efficiency in injecting holes from the hole-injecting layer to the light-emitting layer improves, and the device is improved in light emission brightness and light emission efficiency. In this case, preferably, for light emission, the light-emitting material itself, used in the light-emitting layer, has the capability of transporting electrons, or the light-emitting layer contains an electron-injecting material. There is another two-layered structure formed of a light-emitting layer and an electron-injecting layer. In this case, preferably, the light-emitting material itself has the capability of injecting holes, or the light-emitting layer contains a hole-injecting material.

In a three-layered structure, the device has a light-emitting layer, a hole-injecting layer and an electron-injecting layer, so that the efficiency in the recombination of holes and electrons in the light-emitting layer is improved. When the organic EL device is formed so as to have a multi-layered structure as described above, the decrease in brightness and the decrease in life caused by quenching can be prevented. In the device having the above multi-layered structure, a light-emitting material, a dopant, a hole-injecting material for transporting a carrier and an electron-injecting material may be used in combination as required. Further, the use of a dopant improves the light emission brightness and the light emission efficiency, and gives red or blue light. Further, any one or each of the hole-injecting layer, the light-emitting layer and the electron-injecting layer may be formed of at least two layers.

As an electrically conductive material for the anode of the organic EL device, it is preferred to use a material having a work function of greater than 4 eV. The electrically conductive material is selected from a metal such as Au, Pt, Ag, Cu or Al, indium tin oxide (ITO), NESA or an organic electrically conductive resin such as polythiophene or polypyrrole.

As an electrically conductive material for the cathode, it is preferred to use a metal or a metal alloy having a work function of smaller than 4 eV. The electrically conductive material is selected from a metal such as Al, In, Mg, Li or Ca, or an alloy such as Mg/Ag, Li/Al or Mg/Al. Any one or each of the anode and the cathode may be formed of two layers or more as required. The anode and the cathode are formed by a known film forming method such as vapor deposition, sputtering, ion plating or plasma manganese.

For the effective light emission of the organic EL device, at least one of the electrodes is desirably sufficiently transparent in the light emission wavelength region of the device. Further, the substrate is desirably transparent. The transparent electrode is produced from the above electrically conductive material by a deposition method or a sputtering method such that a predetermined permeability to light is secured. The electrode which forms a light emission surface preferably has a light transmittance of at least 10%.

The substrate is not specially limited so long as it has mechanical and thermal strength and is transparent. For example, it is selected from glass substrates and substrates of transparent resins such as a polyethylene substrate, a polyether sulfone substrate and a polypropylene polyimide substrate. The substrate may have any form such as the form of a plate or a film.

Each of the layers forming the organic EL device of the present invention can be formed by any one of dry film forming methods such as a vacuum deposition method and a sputtering method and wet film forming methods such as a spin coating method and a dipping method. The thickness of each layer is not specially limited, while each layer is required to have a proper thickness. When the layer thickness is too large, inefficiently, a high voltage is required to achieve predetermined emission of light. When the layer thickness is too small, the layer is liable to have a pinhole, etc., so that no sufficient light emission brightness can be obtained even when an electric field is applied. Generally, the thickness of each layer is preferably in the range of from 5 nm to 10 $\mu$m, more preferably 10 nm to 0.2 $\mu$m.

In the wet film forming method, a material for forming an intended layer is dissolved or dispersed in a proper solvent such as chloroform, tetrahydrofuran or dioxane, and a thin film is formed from the solution or dispersion. The solvent shall not be limited to these. For improving the film formability and preventing the occurrence of pinholes, the above solution or dispersion for forming the layer may contain a proper resin and a proper additive.

The resin for use in the present invention includes insulating resins such as polystyrene, polycarbonate, polyarylate, polyester, polyamide, polyurethane, polysulfone, polymethyl methacrylate, polymethyl acrylate and cellulose, photo-conductive resins such as poly-N-vinylcarbazole and polysilane, and electrically conductive resins such as polythiophene and polypyrrole. The above additive includes an antioxidant, an ultraviolet absorbent and a plasticizer.

Examples of the light-emitting material or the dopant which is usable in the organic EL device of the present invention include anthracene, naphthalene, phenanthrene, pyrene, tetracene, coronene, chrysene, fluorescein, perylene, phthaloperylene, naphthaloperylene, perinone, phthaloperinone, naphthaloperinone, diphenylbutadiene, tetraphenylbutadiene, coumarine, oxadiazole, aldazine, bisbenzoxazoline, bisstyryl, pyrazine, cyclopentadiene, quinoline metal complex, aminoquinoline metal complex, benzoquinoline metal complex, imine, diphenylethylene, vinyl anthracene, diaminocarbazole, pyran, thiopyran, polymethine, merocyanine, an imidazole-chelated oxynoid compound, quinacridone, rubrene and derivatives of these, while the light-emitting layer or the dopant shall not be limited to the above materials.

The hole-injecting material which can be used in combination with the material of the present invention includes compounds which have the capability of transporting holes, exhibit an effect on the injection of holes to a light-emitting layer or a light-emitting material, prevent the migration of excitons generated in a light-emitting layer into an electron-injecting layer and have the excellent capability of forming a thin film. Specific examples of the hole-injecting material include a phthalocyanine derivative, a naphthalocyanine-containing compound, a porphyrin-containing compound, oxadiazole, triazole, imidazole, imidazolone, imidazolthione, pyrazoline, pyrazolone, tetrahydroimidazole, oxazole, hydrazone, acylhydrazone, polyarylalkane, stilbene, butadiene, benzidine type triphenylamine, styrylamine type triphenylamine, diamine type triphenylamine, derivatives of these, and polymer materials such as polyvinylcarbazole, polysilane and an electrically conductive polymer. However, the hole-injecting material shall not be limited to the above materials.

The electron-injecting material includes materials which are capable of injecting electrons, exhibit an effect on the injection of electrons into a light-emitting layer or a light-emitting material, prevent the migration of excitons generated in the light-emitting layer into the hole-injecting layer and have the excellent capability of forming a thin film. Examples of the electron-injecting material include fluorenone, anthraquinodimethane, diphenoquinone, thiopyran dioxide, oxadiazole, perylenetetracarboxylic acid, fluorenylidenemethane, anthrone, and derivatives of these. However, the electron-injecting material shall not be limited to these. The hole-injecting material can be sensitivity-increased by adding an accepter material thereto, and the electron-injecting material can be sensitivity-increased by adding an doner material.

The material of the present invention can be used in any layer of the organic EL device, and the material of the present invention and at least one of a light-emitting material, a dopant, a hole-injecting material and an electron-injecting material may be contained in one layer.

Further, the organic EL device of the present invention may be improved in stability against temperature, humidity and atmosphere by forming a protective layer on its surface, or by protecting the entire device with a silicon oil.

In the present invention, the light emission efficiency and the light emission brightness can be improved by the use of the material of the present invention. Further, the organic EL device of the present invention is stable against heat and electric current and gives a practically acceptable light emission brightness at a low driving voltage, so that it excellently overcomes the degradation which has been a conventional big problem.

The organic EL device of the present invention can be applied to flat panel displays such as an on-wall television set, a flat light-emitting device, a light source for a copying machine or a printer, a light source for a liquid crystal display or a counter, a display signboard and a signal light, and it therefore has high industrial values.

The present invention provides materials which have the excellent capability of injecting holes. The material of the present invention can give an organic EL device which has a higher light emission efficiency and a higher brightness and a longer device life than any conventional device.

EXAMPLES

The present invention will be explained more in detail with reference to Examples hereinafter. In Examples, "part" stands for "part by weight".

Method of Synthesis of Compound (3)

10 Parts of tris(p-bromophenyl)amine, 35 parts of 4,4-diisopropyl(2-phenyl)diphenylamine, 12 parts of potassium carbonate and 0.5 part of a copper powder were added to 50 parts of 1,3-dimethyl-2-imidazolidinone, and the mixture was stirred under heat at 200° C. for 50 hours. Then, the reaction mixture was diluted with 500 parts of water. The mixture was extracted with ethyl acetate, and the extract was concentrated, and purified by silica gel column chromatography to give 15 parts of a powder having white fluorescence. The powder was analyzed by FD-MS for a molecular weight to show that it was Compound (3).

FIG. 1 shows the infrared absorption spectrum (KBr tablet method) of Compound (3).

DSC analysis of Compound (3) showed that it had a glass transition temperature of 140° C., a melting point of 300° C. or higher and a decomposition temperature of 400° C. or higher. Compound (3) has a glass transition temperature higher than those of TDATA and MTDATA by 50 to 70° C., a melting point higher than those of TDATA and MTDATA by at least 100° C., and a decomposition temperature higher than those of TDATA and MTDATA by at least 50° C. All the compounds of the formula (1), (6) and (7) have glass transition temperatures, melting points and decomposition temperatures similar to those of Compound (3) or excellent thermal properties over those of Compound (3), and these compounds have high heat resistance as hole-transporting materials for an organic EL device.

Method of Synthesis of Compound (5)

8 Parts of tris(p-bromophenyl)amine, 25 parts of 4,4'-(phenoxy)diphenylamine, 10 parts of potassium carbonate and 0.5 part of a copper powder were added to 30 parts of 1,3-dimethyl-2-imidazolidinone, and the mixture was stirred under heat at 200° C. for 50 hours. Then, the reaction mixture was diluted with 500 parts of water. The mixture was extracted with ethyl acetate, and the extract was concentrated, and purified by silica gel column chromatography to give 15 parts of a powder having white fluorescence. The powder was analyzed by FD-MS for a molecular weight to show that it was Compound (5).

Method of Synthesis of Compound (19)

5 Parts of 1,3,6-triiodobenzene, 20 parts of 4,4'-(phenoxy)diphenylamine, 8 parts of potassium carbonate and 0.5 part of a copper powder were added to 20 parts of nitrobenzene, and the mixture was stirred under heat at 200° C. for 50 hours. Then, the reaction mixture was diluted with 500 parts of water. The mixture was extracted with ethyl acetate, and the extract was concentrated, and purified by silica gel column chromatography to give 3 parts of a powder having white fluorescence. The powder was analyzed by FD-MS for a molecular weight to show that it was Compound (19).

Method of Synthesis of Compound (24)

5 Parts of 1,3,6-triiodobenzene, 28 parts of 4-(1-naphthoxy)-4'-(phenoxy)diphenylamine, 12 parts of potassium carbonate and 0.5 part of a copper powder were added to 20 parts of nitrobenzene, and the mixture was stirred under heat at 200° C. for 50 hours. Then, the reaction mixture was diluted with 500 parts of water. The mixture was extracted with ethyl acetate, and the extract was concentrated, and purified by silica gel column chromatography to give 3 parts of a powder having white fluorescence. The powder was analyzed by FD-MS for a molecular weight to show that it was Compound (24).

Example 1

Tris(8-hydroxyquinoline)aluminum complex, Compound (1) and a polycarbonate resin (Panlite L-1250, supplied by Teijin Kasei) in an amount ratio of 3:2:5 were dissolved and dispersed in chloroform, and the solution was spin-coated on a cleaned glass substrate with an ITO electrode to form a light-emitting layer having a thickness of 100 nm. An electrode having a thickness of 150 nm was formed thereon from a magnesium/silver alloy having a magnesium/silver mixing ratio of 10/1, to obtain an organic EL device. The device showed a light emission brightness of 80 cd/m$^2$ at a direct current voltage of 5 V and a light emission efficiency of 0.6 lm/W.

Example 2

Compound (1) was vacuum-deposited on a cleaned glass substrate with an ITO electrode, to obtain a hole-injecting layer having a thickness of 30 nm. Then, tris(8-hydroxyquinoline)aluminum complex was vacuum-deposited to form a light-emitting layer having a thickness of 50 nm. Further, an electrode having a thickness of 150 nm was formed thereon from a magnesium/silver alloy having a magnesium/silver mixing ratio of 10/1, to obtain an organic EL device. The above hole-injecting layer and the light-emitting layer were formed by vapor deposition under a vacuum of 10$^{-6}$ Torr at a substrate temperature of room temperature. The device showed a light emission brightness of about 210 cd/m$^2$ at a direct current voltage of 5 V and a light emission efficiency of 1.5 lm/W.

Example 3

Compound (2) was vacuum-deposited on a cleaned glass substrate with an ITO electrode, to obtain a hole-injecting layer having a thickness of 30 nm. Then, 4,4'-bis[N-(1-naphthyl)-N-phenylamino]biphenyl (α-NPD) was vacuum-deposited to form a second hole-injecting layer having a thickness of 10 nm. Further, Compound (28) having the following structural formula was vacuum-deposited to form a light-emitting layer having a thickness of 50 nm, and further, 2-(4-tert-butylphenyl)-5-(biphenyl)-1,3,4-oxadiazole was vacuum-deposited to form an electron-injecting layer having a thickness of 20 nm. An electrode having a thickness of 150 nm was formed thereon from a magnesium/silver alloy having a magnesium/silver mixing ratio of 10/1, to obtain an organic EL device. The device showed a light emission brightness of about 220 cd/m$^2$ at a direct current voltage of 5 V and a light emission efficiency of 2.0 lm/W.

Example 4

Compound (14) was vacuum-deposited on a cleaned glass substrate with an ITO electrode, to obtain a hole-injecting layer having a thickness of 30 nm. Then, 4,4'-bis[N-(1-naphthyl)-N-phenylamino]biphenyl (α-NPD) was vacuum-deposited to form a second hole-injecting layer having a thickness of 10 nm. Further, Compound (28) having the following structural formula was vacuum-deposited to form a light-emitting layer having a thickness of 50 nm, and further, Compound (15) was vacuum-deposited to form an electron-injecting layer having a thickness of 20 nm. An electrode having a thickness of 150 nm was formed thereon from a magnesium/silver alloy having a magnesium/silver mixing ratio of 10/1, to obtain an organic EL device. The device showed a light emission brightness of about 320 cd/m$^2$ at a direct current voltage of 5 V and a light emission efficiency of 3.0 lm/W.

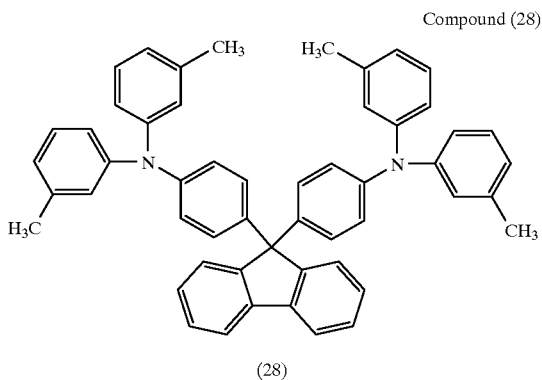

Compound (28)

Example 5

Compound (3) was vacuum-deposited on a cleaned glass substrate with an ITO electrode, to obtain a hole-injecting layer having a thickness of 30 nm. Then, 4,4'-bis[N-(1-naphthyl)-N-phenylamino]biphenyl (α-NPD) was vacuum-deposited to form a second hole-injecting layer having a thickness of 10 nm. Further, Compound (29) having the following structural formula was vacuum-deposited to form a light-emitting layer having a thickness of 50 nm, and further, an electron-injecting layer having a thickness of 50 nm was formed from tris(8-hydroxyquinoline)aluminum complex. An electrode having a thickness of 150 nm was formed thereon from a magnesium/silver alloy having a magnesium/silver mixing ratio of 10/1, to obtain an organic EL device. The device showed a light emission brightness of about 430 cd/m² at a direct current voltage of 5 V and a light emission efficiency of 2.6 lm/W.

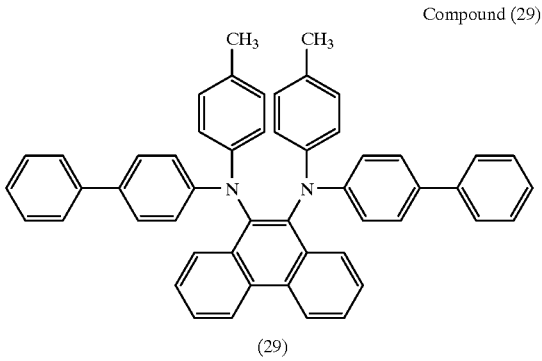

Compound (29)

Example 6

Compound (3) was vacuum-deposited on a cleaned glass substrate with an ITO electrode, to obtain a hole-injecting layer having a thickness of 30 nm. Then, 4,4'-bis[N-(1-naphthyl)-N-phenylamino]biphenyl (α-NPD) was vacuum-deposited to form a second hole-injecting layer having a thickness of 10 nm. Further, N,N,N',N'-[4-(α,α-dimethylbenzyl)phenyl]-anthranyl-9,10-diamine was vacuum-deposited to form a light-emitting layer having a thickness of 50 nm, and further, an electron-injecting layer having a thickness of 50 nm was formed from tris(8-hydroxyquinoline)aluminum complex. An electrode having a thickness of 150 nm was formed thereon from a magnesium/silver alloy having a magnesium/silver mixing ratio of 10/1, to obtain an organic EL device. The device showed a light emission brightness of about 510 cd/m² at a direct current voltage of 5 V and a light emission efficiency of 4.6 lm/W.

Examples 7–32

Compound shown in Table 2 was vacuum-deposited on a cleaned glass substrate with an ITO electrode, to obtain a hole-injecting layer having a thickness of 30 nm. Then, 4,4,-bis[N-(1-naphthyl)-N-phenylamino]biphenyl (α-NPD) was vacuum-deposited to form a second hole-injecting layer having a thickness of 10 nm. Further, Compound (29) was vacuum-deposited to form a light-emitting layer having a thickness of 50 nm, and further, Compound (30) having the following structural formula was vacuum-deposited to form an electron-injecting layer having a thickness of 50 nm. An electrode having a thickness of 150 nm was formed thereon from a magnesium/silver alloy having a magnesium/silver mixing ratio of 10/1, to obtain an organic EL device. The device showed a light emission brightness shown in Table 2 at a direct current voltage of 5 V and a light emission efficiency shown in Table 2.

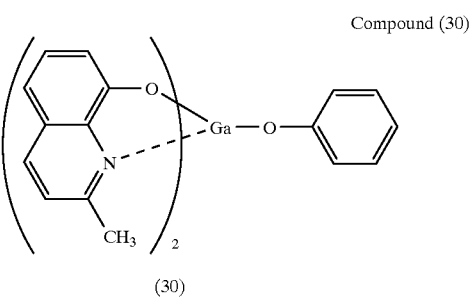

Compound (30)

TABLE 2

| Example | Compound | Light emission brightness (cd/m²) | Light emission efficiency (1 m/W) |
| --- | --- | --- | --- |
| 7 | (1) | 430 | 3.2 |
| 8 | (2) | 450 | 3.7 |
| 9 | (3) | 500 | 3.9 |
| 10 | (4) | 480 | 3.5 |
| 11 | (5) | 350 | 3.2 |
| 12 | (6) | 390 | 3.3 |
| 13 | (7) | 450 | 3.4 |
| 14 | (8) | 420 | 3.3 |
| 15 | (9) | 460 | 3.6 |
| 16 | (10) | 500 | 3.9 |
| 17 | (11) | 500 | 3.9 |
| 18 | (12) | 500 | 4.0 |
| 19 | (13) | 420 | 3.6 |
| 20 | (14) | 430 | 3.1 |
| 21 | (15) | 460 | 3.8 |
| 22 | (16) | 430 | 3.6 |
| 23 | (17) | 410 | 3.9 |
| 24 | (18) | 410 | 4.5 |
| 25 | (19) | 450 | 3.6 |
| 26 | (20) | 430 | 3.3 |
| 27 | (21) | 460 | 4.1 |
| 28 | (22) | 420 | 3.6 |
| 29 | (23) | 490 | 3.9 |
| 30 | (24) | 350 | 3.2 |
| 31 | (25) | 320 | 3.6 |
| 32 | (26) | 380 | 3.0 |

Comparative Example 1

An organic EL device was prepared in the same manner as in Example 4 except that 4,4',4"-tris[N-(3-methylphenyl)-

N-phenylamino]triphenylamine was used for forming a hole-injecting layer.

The device showed a light emission brightness of about 190 cd/m² at a direct current voltage of 5 V and a light emission efficiency of 1.58 lm/W.

When the organic EL devices obtained in the above Examples were allowed to continuously emit light at 3 mA/cm², all the organic EL devices emitted light with a brightness of more than 50% of the initial brightness value for more than 1,000 hours. When the organic EL device obtained in Comparative Example 1 was allowed to continuously emit light under the same conditions, the light emission brightness of the organic EL device decreased to less than 50% of the initial brightness value in 100 hours, and further, the number of dark spots extremely increased.

The organic EL device of the present invention accomplishes improvements in light emission efficiency and light emission brightness and a longer device life, and does not impose any limitations on a light-emitting material, a dopant, a hole-injecting material, an electron-injecting material, a sensitizer, a resin and an electrode material used in combination and the method of producing the device.

What is claimed is:

1. A material for an organic EL device, which has the formula (1),

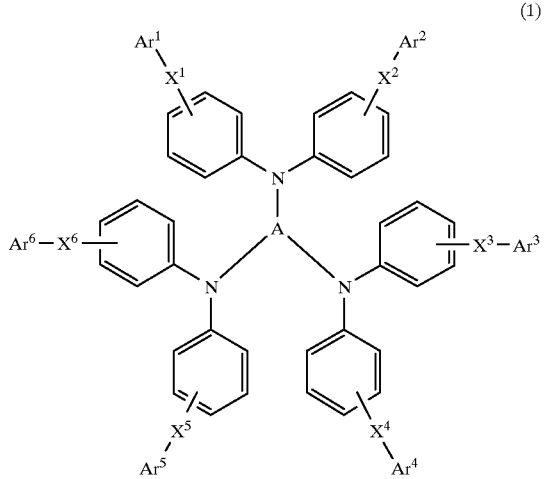

(1)

wherein each of $Ar^1$ to $Ar^6$ is independently a substituted or non-substituted aryl group, each of $X^1$ to $X^6$ is independently —$(CH_2)_x$—O—$(CH_2)_y$—, a substituted or non-substituted alkylene group or a substituted or non-substituted alicyclic moiety, in which each of x and y is an integer of 0 to 20, provided that x+y=0 in no case, and A is a group having one of the following formulae,

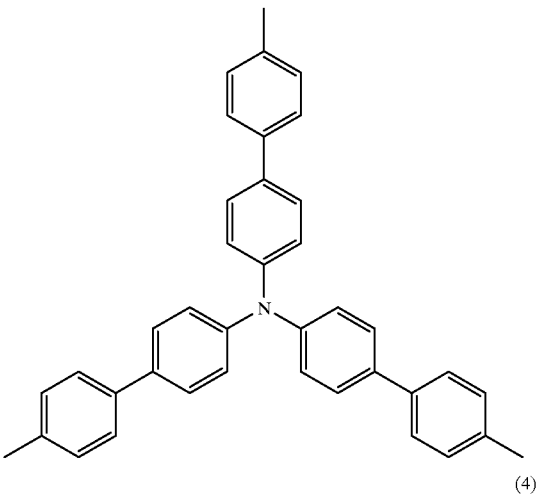

(2)

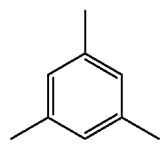

(3)

(4)

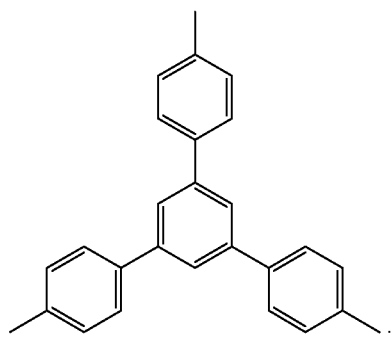

(5)

2. A material according to claim 1, wherein the material having the formula (1), is a hole-injecting material.

3. A material according to claim 1, wherein A of the formula (1) is a compound of formula (2).

4. An organic electroluminescence device obtained by forming a light-emitting layer or a plurality of organic compound layers including the light-emitting layer between a pair of electrodes composed of a cathode and an anode, wherein at least one layer contains the material recited in claim 1 as a hole-injecting material.

5. A device according to claim 4, wherein the organic layer formed between the anode and the light-emitting layer contains the material recited in claim 1.

6. A device according to claim 4, wherein the organic layer present between the anode and the light-emitting layer is formed of at least two hole-injecting layers and the hole-injecting layers contain the material recited in claim 1 as a hole-injecting material.

7. A device according to claim 4, wherein the light-emitting layer contains the material recited in claim 1 as a hole-injecting material.

* * * * *